US012221651B2

(12) United States Patent
Armstrong et al.

(10) Patent No.: US 12,221,651 B2
(45) Date of Patent: Feb. 11, 2025

(54) POLYNUCLEOTIDE DETECTION SYSTEM

(71) Applicant: The United States of America, as represented by the Secretary of Agriculture, Washington, DC (US)

(72) Inventors: Cheryl M. Armstrong, Abington, PA (US); Joseph A. Capobianco, Jr., Marlton, NJ (US); Andrew G. Gehring, Resher, PA (US); Joseph Lee, Flemington, NJ (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 290 days.

(21) Appl. No.: 17/217,495

(22) Filed: Mar. 30, 2021

(65) Prior Publication Data

US 2022/0325329 A1    Oct. 13, 2022

(51) Int. Cl.
*C12Q 1/6825* (2018.01)
*B01L 3/00* (2006.01)
*C12Q 1/689* (2018.01)

(52) U.S. Cl.
CPC ........ *C12Q 1/6825* (2013.01); *B01L 3/50273* (2013.01); *B01L 3/502738* (2013.01); *C12Q 1/689* (2013.01)

(58) Field of Classification Search
CPC .... C12Q 1/6825; C12Q 1/689; C12Q 1/6816; C12Q 2565/519; C12Q 2565/607; B01L 3/50273; B01L 3/502738; B01L 3/5027; G01N 33/5308; G01N 33/5438; G01N 27/3276
See application file for complete search history.

(56) References Cited

U.S. PATENT DOCUMENTS

| 2005/0136500 | A1* | 6/2005 | Yang ................. G01N 33/5438 436/514 |
| 2010/0000881 | A1 | 1/2010 | Franzen |
| 2010/0173305 | A1* | 7/2010 | Reshatoff ............. C12Q 1/6816 435/6.15 |
| 2014/0274805 | A1* | 9/2014 | Wohlstadter ......... C12Q 1/6825 506/18 |
| 2014/0287411 | A1 | 9/2014 | Reshatoff et al. |
| 2017/0111202 | A1 | 4/2017 | Kim et al. |
| 2018/0015474 | A1* | 1/2018 | Arlett ............... G01N 35/00029 |
| 2020/0300801 | A1 | 9/2020 | Capobianco et al. |

FOREIGN PATENT DOCUMENTS

| KR | 20160021673 A | 8/2014 |
| WO | 9628538 | 9/1996 |

OTHER PUBLICATIONS

C.M. Armstrong, et al., 2021, "Flow-through electrochemical biosensor for the detection of Listeria monocytogenes using oligonucleotides," Sensors: 21, Article No. 3754, pp. 1-15.
L. Beaudet, et al., 2001 "Homogeneous assays for single-nucleotide polymorphism typing using AlphaScreen," Genome Res. 11(4): 600-608.
J.A. Capobianco, et al., 2019, "Rapid detection of Salmonella enterica serotype Typhimurium in large volume samples using porous electrodes in a flow-through, enzyme-amplified immunoelectrochemical sensor," Analytical and Bioanalytical Chemistry 411: 5233-5242.
J.A. Capobianco, et al., 2021, "Detection of pathogenic bacteria in large volume food samples using an enzyme-linked immunoelectrochemical biosensor," Food Control 119 107456; available online Jul. 2, 2020.
D. Dressman, et al., 2003, "Transforming single DNA molecules into fluorescent magnetic particles for detection and enumeration of genetic variations," Proc. Natl. Acad. Sci. U. S. A. 100(15): 8817-8822.
P. Glaser, et al., 2001, "Comparative genomics of Listeria species," Science 294(5543): 849-852.
M. Santhanam, et al., 2020, "DNA/RNA electrochemical biosensing devices a future replacement of PCR methods for a fast epidemic containment," Sensors 20: 1-15, article No. 4648, pp. 1-15.
R.F. Wang, et al., 1992, "16S rRNA-based probes and polymerase chain reaction method to detect Listeria monocytogenes cells added to foods," Applied and Environmental Microbiology 58 (9): 2827-2831.
International Search Report on PCT/US2022/022163 dated Mar. 28, 2022.
International Searching Authority Written Opinion on PCT/US2022/022163 dated Jul. 15, 2022.
C-H Yi, et al., 1996, "Improvement of polymerase chain reaction methods for rapid detection of Listeria monocytogenes in raw milk," Korean J. Vet. Res. 36(1):119-129.

(Continued)

*Primary Examiner* — Narayan K Bhat
(74) *Attorney, Agent, or Firm* — John D. Fado; Richard D. Tuminello

(57) ABSTRACT

A flow-through electrochemical detection system determines if a target nucleic acid polymer is present in a sample. This system contains, at a minimum, an assay reaction chamber that contains a porous working electrode to which target nucleic acid polymer capturing molecules are bound. As a sample passes through the working electrode, any target nucleic acid polymer present in the sample binds to the target nucleic acid polymer capturing molecules. After the sample passes through the flow-through electrochemical detection system, target nucleic acid polymer detectors are placed inside the assay reaction chamber and bind to any target nucleic acid polymer present. The target nucleic acid polymer detectors contain a means for generating an electric current when exposed to a chemical or an enzyme. A potentiostat connected to the working electrode measures the generated current, thereby detecting the presence and quantity of the target nucleic acid polymer in the sample.

18 Claims, 9 Drawing Sheets

Specification includes a Sequence Listing.

(56) References Cited

OTHER PUBLICATIONS

Fragoso et al., Electrochmical immunosensor for detection of proteic cancer markers. Chap. 33, Biosensors and Molecular Technologies 2012.

\* cited by examiner

```
              1                                                             60
SEQ ID NO: 1: GAU G GUACAAAGGGUCGCGAAGCCGCGAGGUGGAGC C AAUCCCAUAAAAC C AUUCUCAGU
SEQ ID NO: 2: GAU G GUACAAAGGGUCGCGAAGCCGCGAGGUGGAGC C AAUCCCAUAAAAC C AUUCUCAGU
SEQ ID NO: 3: GAU A GUACAAAGGGUCGCGAAGCCGCGAGGUGGAGC U AAUCCCAUAAAAC U AUUCUCAGU 61                                                            120
SEQ ID NO: 1: UCGGAUUGUAGGCUGCAACUCGCCUACAUGAAGCCGGAAUCGCUAGUAAUCG C GGAUCAG
SEQ ID NO: 2: UCGGAUUGUAGGCUGCAACUCGCCUACAUGAAGCCGGAAUCGCUAGUAAUCG U GGAUCAG
SEQ ID NO: 3: UCGGAUUGUAGGCUGCAACUCGCCUACAUGAAGCCGGAAUCGCUAGUAAUCG U GGAUCAG
```

FIG. 6

POLYNUCLEOTIDE DETECTION SYSTEM

FIELD OF THE INVENTION

The invention pertains to a detection system that can determine the presence of at least one target nucleic acid polymer in a sample using a chemical or enzymatic reaction that generates a measurable electric current when the target nucleic acid polymer is present. The sample traverses through a porous electrode to which target nucleic acid polymer-capturing molecules are attached, and which bind the target nucleic acid polymer. Because a large quantity of the sample can pass through the porous membrane, minute quantities of a target polynucleotide in the sample are able to be captured by the system and thereby are detected. Using this system, it is possible to specifically detect target nucleic acid polymers, even if they have high similarity to other nucleic acid polymers in the sample.

SEQUENCE LISTING

The instant application contains a Sequence Listing which has been submitted via EFS-Web as ASCII compliant text file format (.txt), and is hereby incorporated by reference in its entirety. The ASCII file was created on Mar. 29, 2021, is named "SequenceListing_ST25", and has 32 bytes. This Sequence Listing serves as paper copy of the Sequence Listing required by 37 C.F.R. § 1.821(c) and the Sequence Listing in computer-readable form (CRF) required by 37 C.F.R. § 1.821(e). A statement under 37 C.F.R. § 1.821(f) is not necessary.

BACKGROUND OF THE INVENTION

Methods for detecting and measuring nucleic acid polymers are well known. However, the current methods are labor intensive and have low sensitivity.

US Publication No. 20200300801 (U.S. application Ser. No. 16/682,719, filed 13 Nov. 2019) describes a testing platform that uses a flow-through, enzyme-amplified immune-electrochemical sensor for testing large sample volumes. This biosensor incorporates the use of an Ag/AgCl reference electrode, a platinum counter electrode, and a working electrode made from graphite felt. In this system, the graphite felt is coated with target-specific antibodies to allow for the selective capture of specific pathogens. Detection is achieved by "sandwiching" targets between capture antibodies and horse radish peroxidase (HRP)-labeled reporter antibodies. This system requires the use of antibodies to the target polynucleotide.

The instant invention teaches a fast and reliable detection method capable of detecting specific target polynucleotides without a reliance on antibodies. The system is capable of detecting minute quantities of a target polynucleotide in both large and small volumes.

SUMMARY OF THE INVENTION

The disclosure is directed to a system for detecting a target nucleic acid polymer in a sample. The system is structured so that as the sample flows through a porous working electrode, nucleic acid polymer-capturing molecules bind to any target nucleic acid polymer present in the sample; target nucleic acid polymer-detecting molecules bind to any target nucleic acid polymer bound to nucleic acid polymer-capturing molecules in a sandwich hybridization format, an electrical current is generated and is transmitted to the electrical measuring device, the presence of the electric current indicating a presence of the target nucleic acid polymer in the sample. The system comprises at least one assay reaction chamber comprising a porous working electrode, an electrical measuring device in communication with the at least one assay reaction chamber, a plurality of target nucleic acid polymer-capturing molecules bound to the porous working electrode and positioned within the assay reaction chamber, and a plurality of target nucleic acid polymer-detecting molecules.

The disclosure is further directed to a method for detecting a target nucleic acid polymer in a sample. The method comprises passing the sample through the assay reaction chamber, where a plurality of target nucleic acid polymer-capturing molecules bound to a porous working electrode bind to any target nucleic acid polymer in the sample. When target nucleic acid polymer-detecting molecules are passed through the working electrode, target nucleic acid polymer-detecting molecules bind to any target nucleic acid polymer bound to the target nucleic acid polymer-capturing molecules bound to the porous working electrode in a sandwich hybridization format, and perform a reaction with the target nucleic acid polymer-detecting molecules to generate an electrical current. The electrical current is measured by the electrical measuring device, indicating the presence of the target nucleic acid polymer in the sample.

The disclosure is also directed to a kit for detecting *Listeria monocytogenes* polynucleotides in a sample. The kit comprises an oligonucleotide that binds at least one *Listeria bacterium*, and an oligonucleotide that specifically binds *L. monocytogenes*. In some embodiments, the oligonucleotide that specifically binds *L. monocytogenes* comprises a nucleotide sequence of SEQ ID NO: 6. In some embodiments, the oligonucleotide that binds at least one *Listeria bacterium* comprises a nucleotide sequence of SEQ ID NO: 5.

The system may further comprise a blocking compound bound to the porous working electrode. The blocking compound may be at least one of bovine serum albumin (BSA), non-fat milk, salmon sperm DNA (SSDNA), sheared SSDNA, or a combination thereof. Alternatively, the system may further comprise a capture molecule binding the target nucleic acid polymer-capturing molecule to the porous working electrode; a flow control valve in fluid communication with the assay reaction chamber, where the flow control valve controls the sample's flow rate through the porous working electrode; a waste reservoir in fluid communication with the flow control valve; a sample reservoir upstream of the assay reaction chamber and in fluid communication with the assay reaction chamber; a filter upstream of the assay reaction chamber in fluid communication with the sample reservoir and the assay reaction chamber; and/or a pump in fluid communication with the assay reaction chamber. The assay reaction chamber may further comprise a reference electrode and a counter electrode. The electrical measuring device in the system may comprise a potentiostat. The target nucleic acid polymer may be RNA, DNA, a mixed nucleotide, an antisense RNA or DNA, a short interfering RNA (siRNA), a microRNA (miRNA), an aptamer, a SPIEGELMER synthetic L-oligonucleotide aptamer, or a peptide nucleic acid.

BRIEF DESCRIPTION OF THE DRAWINGS

FIG. 6 depicts a nucleotide alignment of the 16S rRNA region from different *Listeria* species.

BRIEF DESCRIPTION OF THE SEQUENCE LISTING

The nucleotide sequences disclosed in the specification, their description, and their assigned sequence identifier are listed below in Table 1:

DETAILED DESCRIPTION OF PREFERRED EMBODIMENTS

Figure 1:
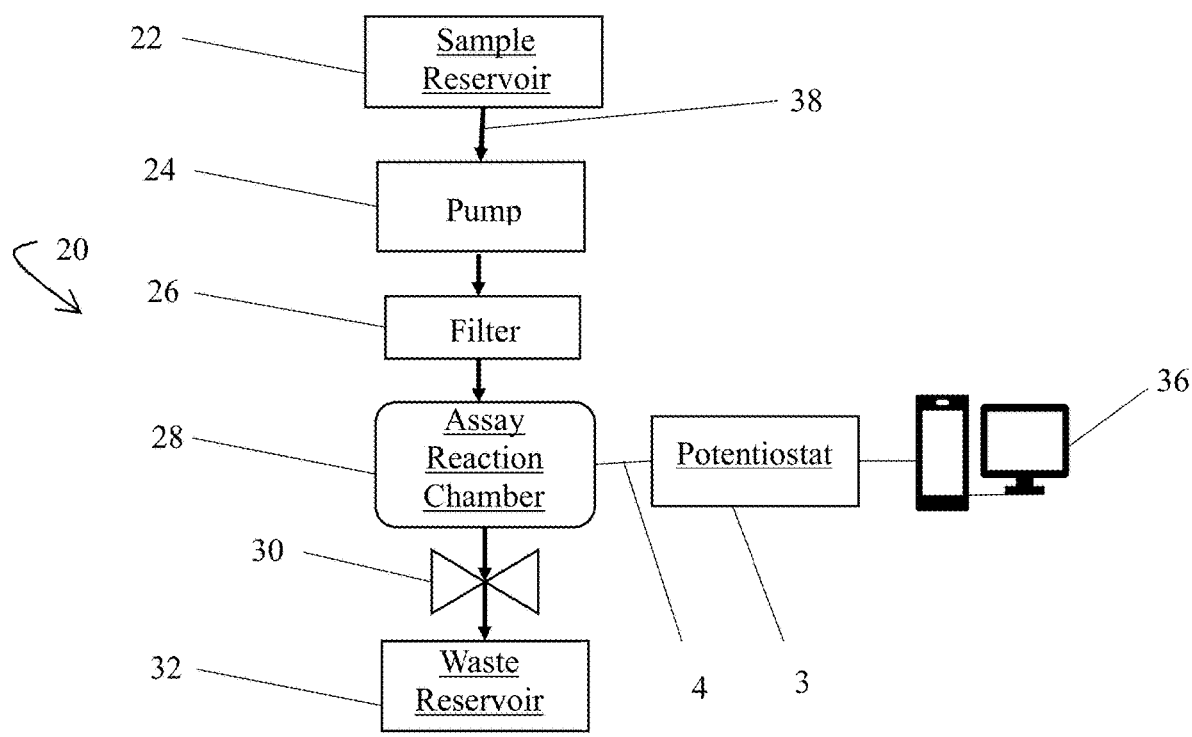
FIG. 1 shows a schematic of one embodiment of the flow-through electrochemical detection system of the invention.

As generally shown in FIG. 1, the system described herein comprises a flow through electrochemical detection system that can determine the presence of at least one target nucleic acid polymer in a sample using a chemical or enzymatic reaction by generating a measurable electric current when the target nucleic acid polymer is present.

As shown in FIG. 1, the flow through electrochemical detection system 20 comprises a sample reservoir 22, a pump 24, a filter 26, at least one assay reaction chamber 28, a flow control valve 30, and a waste reservoir 32, all of which are in fluid communication with each other via a plurality of pipes 38 through which a sample passes. The assay reaction chamber 28 is in electronic communication with a potentiostat 34, which is in electronical communication with a computer processor and associated display 36 through connectors 40. Any means of electronic communication known in the art may be used for the connectors 40, such as wires, or wireless communication. In an alternative embodiment, the pump 24 and filter 26 are optional. In some embodiments, the sample reservoir 22 may be a distinct container holding a sample, a lake, a river, a stream, a waste pond, a cooling pond, or a mine. The flow control valve 30 controls the speed of the sample through the assay reaction chamber 28. In the embodiment shown in FIG. 1, the flow control valve 30 is downstream of the assay reaction chamber 28. In another embodiment the flow control valve 30 can be upstream of the assay reaction chamber 28. The pump 24

TABLE 1

| SEQ ID NO | Name | Sequence |
|---|---|---|
| 1 | L. ivanovii 16S rRNA region | GAUGGUACAAAGGGUCGCGAAGCCGCGAGGUGG AGCCAAUCCCAUAAAACCAUUCUCAGUUCGGAU UGUAGGCUGCAACUCGCCUACAUGAAGCCGGAA UCGCUAGUAAUCGCGGAUCAG |
| 2 | L. innocua 16S rRNA region | GAUGGUACAAAGGGUCGCGAAGCCGCGAGGUGG AGCCAAUCCCAUAAAACCAUUCUCAGUUCGGAU UGUAGGCUGCAACUCGCCUACAUGAAGCCGGAA UCGCUAGUAAUCGUGGAUCAG |
| 3 | L. monocytogenes 16S rRNA region | GAUAGUACAAAGGGUCGCGAAGCCGCGAGGUGG AGCUAAUCCCAUAAAACUAUUCUCAGUUCGGAU UGUAGGCUGCAACUCGCCUACAUGAAGCCGGAA UCGCUAGUAAUCGUGGAUCAG |
| 4 | F-2 Link (Biotin) | CCCCCTAATCCCATAAAACTATTCT |
| 5 | L. mono_16S-Rev7 (5Biotin) | CTGATCCACGATTACTAGCGAT |
| 6 | L-2 (HRP) | AGAATAGTTTTATGGGATTAG |
| 7 | L. innocua_16S-Seq (1134-1328) | GACGTCAAATCATCATGCCCCTTATGACCTGGGCT ACACACGTGCTACAATGGATGGTACAAAGGGTCG CGAAGCCGCGAGGTGGAGCCAATCCCATAAAACC ATTCTCAGTTCGGATTGTAGGCTGCAACTCGCCTA CATGAAGCCGGAATCGCTAGTAATCGTGGATCAG CATGCCACGGTGAATACGTTCCC |
| 8 | L. mono_16S-Seq (1193-1387) | GACGTCAAATCATCATGCCCCTTATGACCTGGGCT ACACACGTGCTACAATGGATAGTACAAAGGGTCG CGAAGCCGCGAGGTGGAGCTAATCCCATAAAACT ATTCTCAGTTCGGATTGTAGGCTGCAACTCGCCTA CATGAAGCCGGAATCGCTAGTAATCGTGGATCAG CATGCCACGGTGAATACGTTCCC | forces the sample to move through the flow-through electrochemical detection system at a desired speed. The pump 24 may be located upstream or downstream of the at least one assay reaction chamber 28. The pump 24 may be any type of positive displacement pump such as a vacuum pump, a pneumatic pump, or a hydraulic driven piston, depending on the viscosity of the sample.

Figure 2:
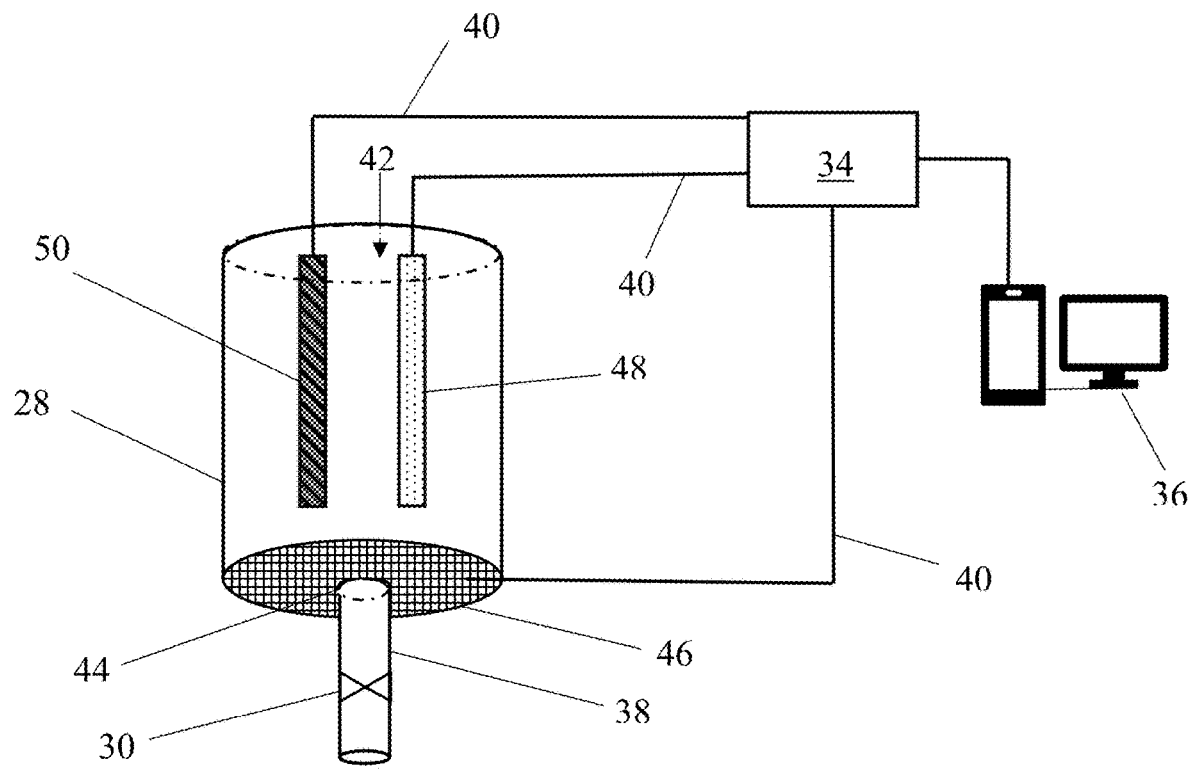
FIG. 2 shows a schematic of the assay reaction chamber in greater detail.

As shown in FIG. 1 and/or FIG. 2, the assay reaction chamber 28, has two openings through which the sample passes, an ingress opening 42 and an egress opening 44. A pipe 38 may be connected to the ingress opening 42 so that the sample can travel from the sample reservoir 22 (shown in FIG. 1) into the assay reaction chamber 28. The sample may be dispensed directly into the assay reaction chamber 28; dispensed directly from the sample reservoir 22 into the assay reaction chamber 28; or dispensed from the sample reservoir 22 through the filter 26. Another pipe 38 is connected to the assay reaction chamber's egress opening 44 and carries the sample to the waste reservoir 32 (shown in FIG. 1). A flow control valve 30 is located in the pipe 38 between the assay reaction chamber's egress opening 44 and the waste reservoir 32 (shown in FIG. 1). The assay reaction chamber 28 contains a working electrode 46 (which is a porous membrane), a counter electrode 48, and a reference electrode 50. These electrodes are in electronic communication, via connectors 40, with the potentiostat 34, which, in turn, is in electronic communication with the computer processor and associated display 36 (shown in FIG. 1). The working electrode 46 spans the assay reaction chamber 28, forming a barrier between the ingress opening 42 and the egress opening 44, and through which the sample must traverse. The working electrode is a porous electron conductive material, and thus an electron transducer. In an embodiment, the working electrode 46 is a polymer containing graphite that percolates (e.g., graphite felt). In an embodiment, the working electrode 46 has a conductivity ranging from approximately 10 (S/m) to approximately $10^7$ (S/m); a porosity ranging from approximately 25% to approximately 90%; and surface area to volume ratio ranging from approximately 0.25 $m^2$/g to approximately 10 $m^2$/g. In some embodiments, the working electrode 46 may be graphite felt, which has an extremely large surface area and contains both functional areas for selective binding, as well as inactive areas.

As shown in FIG. 2, the working electrode 46 is located on or near the bottom of the assay reaction chamber 28 surrounding the egress opening 44. In another embodiment, the working electrode can be located some distance from the bottom of the assay reaction chamber. In either embodiment, one may want to have a finite distance between the working electrode 46 and the other two electrodes (counter electrode 48 and reference electrode 50) to prevent a short circuit from occurring. The counter electrode 48 and the reference electrode 50 may be screen-printed on the inside wall of the assay reaction chamber 28 such that they are partially or fully submerged in the sample above the working electrode 46, and are separated by a finite distance from the working electrode. In an embodiment, the connector 40 is an electrical lead screen-printed along the inside wall of the assay reaction chamber and serves as a means of electronic communication between the working electrode 46 and the potentiostat 34.

In an embodiment, the assay reaction chamber 28 contains one opening in its wall for each electrode present so that each electrode can be in electronic communication with the potentiostat 34 via a connector 40. A via is an electrical connection between layers in a physical electronic circuit that goes through the plane of one or more adjacent layers. The fill material in each opening or via may be electrically conductive. In an embodiment, the via fill material is a conductive epoxy such as a thermoset plastic matrix that is filled with conductive particles, such as, but not limited to, graphite, silver, copper, gold, and graphene. In an embodiment, a through via is used, such as those from Tech-Etch (Plymouth, Massachusetts, USA). In an embodiment, a bonding pad is screen-printed over each electronic fill material on the outside of the assay reaction chamber 28. Each bonding pad is situated to be in electronic contact with a spring-loaded connector. The spring-loaded connector is in electronic communication with a potentiostat 34. In an embodiment, the flow-through electrochemical detection system has a different electrode pattern and with other electronic communication means for connecting to the potentiostat 34.

The flow-through electrochemical detection system 20 can have one assay reaction chamber 28 (as shown in FIG. 1 and FIG. 2), or multiple assay reaction chambers that are in parallel or series orientation to each other. If multiple assay reaction chambers are present, each assay reaction chamber is independently connected to the potentiostat 34. When multiple assay reaction chambers 28 are being used, each assay reaction chamber can assay for a different target nucleic acid polymer 60 and may use the same or different target nucleic acid polymer capturing molecule labels 56, a different target nucleic acid polymer capturing molecule 58, and different target nucleic acid polymer detecting molecules with the same or a different target nucleic acid polymer detecting molecule labels. Thus, the flow-through electrochemical detection system can assay for multiple target nucleic acid polymers at the same time.

Figure 3:
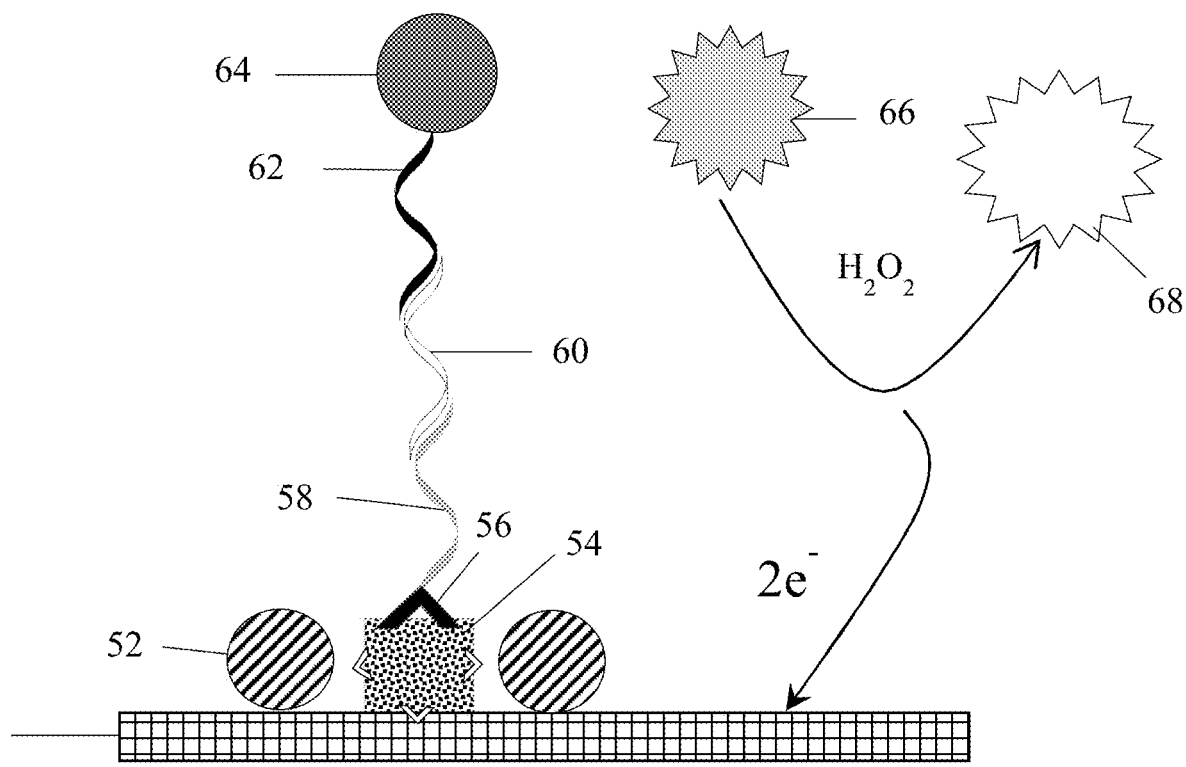
FIG. 3 depicts a schematic of an assay taking place at the surface of the working electrode.

As shown in FIG. 3, bound to the working electrode 46 are blocking compounds 52, and a capture molecule 54. The capture molecule 54 may be a polypeptide, such as NEUTRAVIDIN deglycosylated avidin or any molecule that may bind target nucleic acid polymer-capturing molecules. The target nucleic acid polymer-capturing molecule 58 is bound to the capture molecule 54 through the target nucleic acid polymer-capturing molecule label 56. When target nucleic acid polymers 60 are present, the target nucleic acid polymer-capturing molecule 58 binds target nucleic acid polymer 60. The target nucleic acid polymer detection molecule 62, presented here as an oligonucleotide, binds to the target nucleic acid polymer 60 bound to the target nucleic acid polymer-capturing molecule 58, and the target nucleic acid polymer detection molecule label 64 allows for a signal to be generated. In an embodiment, the target nucleic acid polymer-capturing molecule 58 is bound directly to the working electrode 46. In another embodiment, the target nucleic acid polymer detection molecule 62 comprises the target nucleic acid polymer detection molecule label 64.

The target nucleic acid polymer detection molecule label 64 may be an enzyme (or protein). The target nucleic acid polymer detection molecule label 64 may be horseradish peroxidase (HRP). HRP can catalyze the oxidation of a wide variety of substrates by $H_2O_2$. In the presence of hydrogen peroxide ($H_2O_2$) HRP facilitates detection of the target nucleic acid polymer detection molecule 62 bound to the target nucleic acid polymer 60 through oxidation of the reduced substrate 66 (presented here as 3,3',5,5'-tetramethylbenzidine (TMB)) to produce oxidized substrate 68, thereby generating an electrical current. The electrons generated contact the working electrode 46, generating an electrical charge that is transmitted through the connectors 40, shown in FIG. 1 and FIG. 2 to the potentiostat 34, and the results displayed in display 36.

Figure 4:
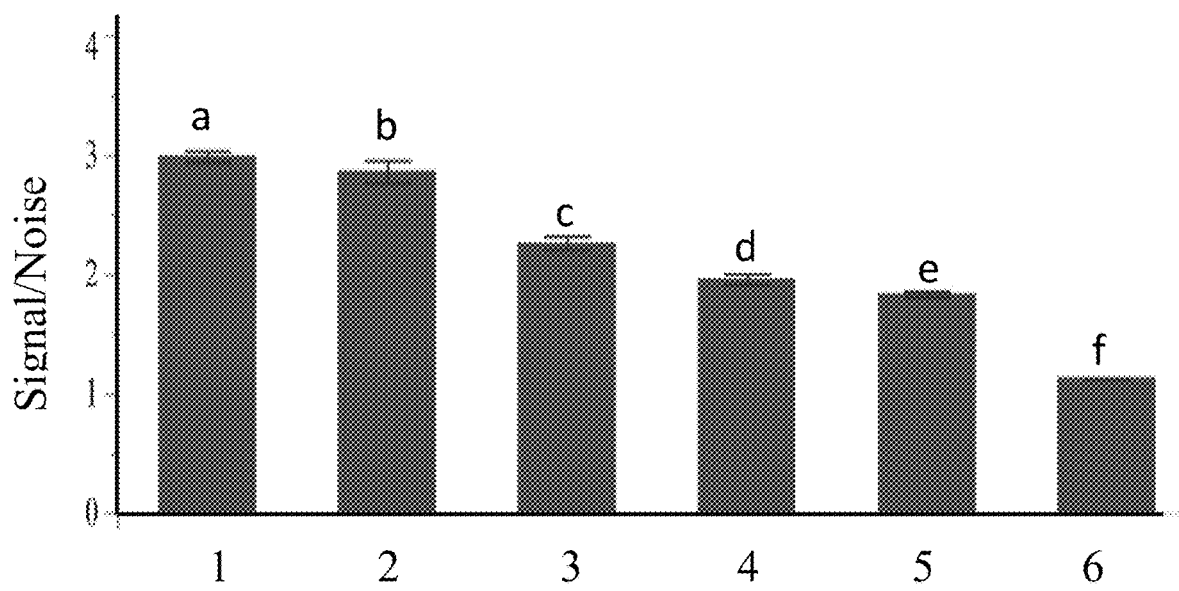
FIG. 4 depicts a graph of the signal-to-noise ratios of electrical currents generated using the flow through electrochemical sensor of the invention and using different blocking compounds.

As shown on FIG. 4, the highest measured electrochemical signal to noise ratio was obtained when using bovine serum albumin (BSA) plus sheared salmon sperm DNA (sheared SSDNA; 1) as a blocking compound. These data were obtained using a flow through electrochemical detection system of FIG. 3, with modifications. The working electrode 46 was coated with target nucleic acid polymer capturing molecules 54 and one of the different blocking compounds to be tested. In the presence of target nucleic acid polymer detecting molecule 62 labeled at its 5' end with horseradish peroxidase (HRP) as target nucleic acid polymer detecting molecule label 64. In the presence of $H_2O_2$ the bound HRP oxidizes the reduced substrate 66 to produce oxidized substrate and electrons, the electrons then contact the working electrode and generate an electrical charge that is transmitted through the connectors 40. The signal to noise ratio of the electrochemical signal obtained for each of the different blocking compounds is shown in the graph. 1: bovine serum albumin (BSA) plus sheared salmon sperm DNA (sheared SSDNA). 2: BSA. 3: sheared SSDNA. 4: Non-fat milk. 5: BSA plus not sheared SSDNA. 6: not sheared SSDNA. The measured electrochemical responses between all of the experimental factors were statistically significant ($0.001 < p < 0.003$). As shown in FIG. 4, the signal to noise ratio of the electrical currents generated using the flow through electrochemical sensor were highest when BSA plus sheared SSDNA was used as the blocking compound (1 in the X axis).

Figure 5:
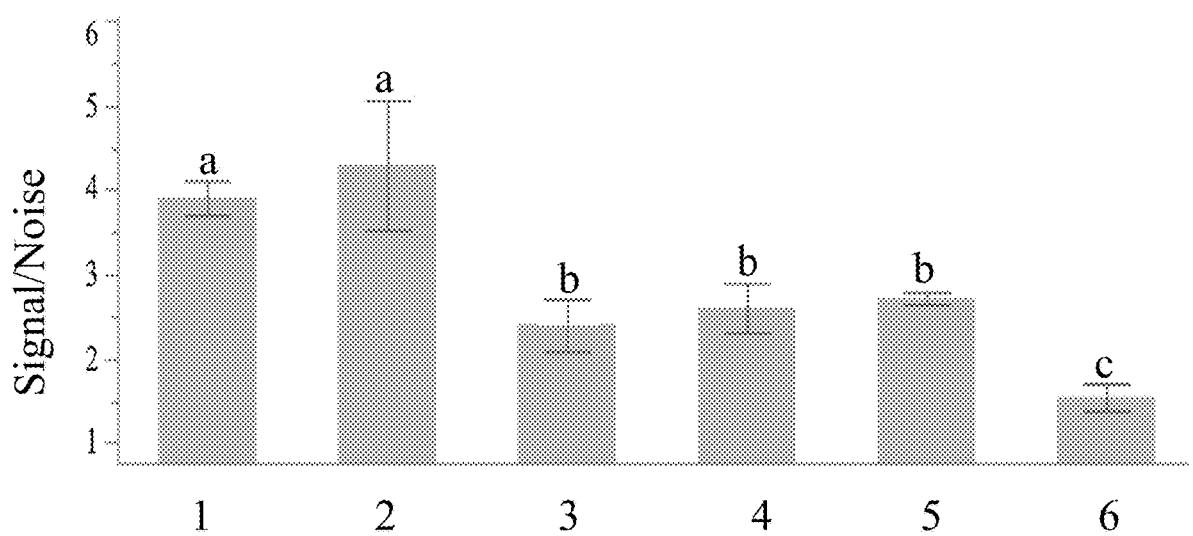
FIG. 5 depicts a graph of the signal-to-noise ratios of the absorbance readings at 450 nm for the same samples measured in FIG. 4.

As shown on FIG. 5, when testing the same blocking compounds as in FIG. 4, the signal to noise ratio of the absorbance readings at 450 nm were highest for BSA plus sheared SSDNA (1) and BSA (2), followed by sheared SSDNA (3), Non-fat milk (4), and BSA plus not sheared SSDNA (5); followed by not sheared SSDNA (6). As can be seen in the figure, several of the absorbance measurements (such as BSA plus sheared SSDNA (1) compared to BSA alone (2) and BSA plus not sheared SSDNA (5) compared to sheared SSDNA (3) or nonfat milk alone (4)) cannot be differentiated by a Students t-test with $p < 0.05$. These data also indicated that while there was a good deal of similarity between the performance of the blocking agents using the flow-through electrochemical sensor and the absorbance readings, the flow-through electrochemical sensor was more sensitive than the absorbance readings to the blocking agent used.

As shown in FIG. 6, alignment of the nucleotide sequence of the 16S rRNA region from *L. ivanovii* (SEQ ID NO: 1), *L. innocua* (SEQ ID NO: 2), and *L. monocytogenes* (SEQ ID NO: 3) indicated that in this 120 nucleotide region *L. monocytogenes* differs from *L. ivanovii* and *L. innocua* by only four nucleotides.

Figure 7:
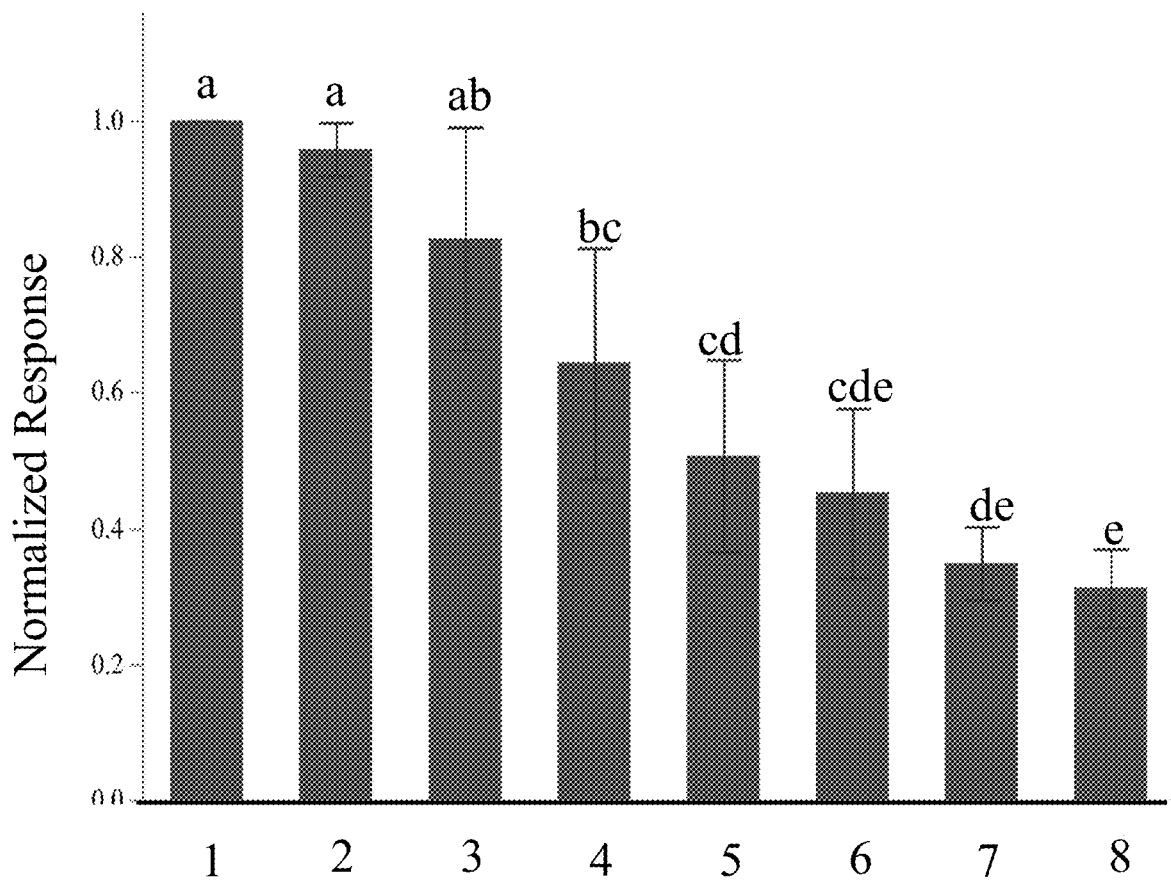
FIG. 7 depicts a graph of the normalized current response measured for assays containing a constant number of polynucleotide-capturing oligonucleotides bound to the surface of the working electrode after exposure to various concentrations of the polynucleotide-detecting molecule.

As shown in FIG. 7, the system is capable of producing an electrical response that is directly dependent on the concentration of the target nucleic acid polymer detecting molecule 62 with a limit of detection of $1 \times 10^{-16}$ M ($p=0.0474$). The data for this figure was obtained by using a flow through electrochemical detection system of FIG. 3, with modifications. The working electrode 46 was coated with BSA plus sheared SSDNA as blocking compound 52, and with capture molecules 54 bound to a constant amount of target nucleic acid polymer capturing molecule label 56 conjugated to the 5'end of the target nucleic acid polymer capturing molecule 58. In the presence of target nucleic acid polymer detecting molecule 62 labeled at its 5' end with horseradish peroxidase (HRP) as target nucleic acid polymer detecting molecule label 64. In the presence of $H_2O_2$ the bound HRP oxidizes the reduced substrate 66 to produce oxidized substrate and electrons which contact the working electrode and generate an electrical charge that is transmitted through the connectors 40. A constant amount ($2.0 \times 10^{-4}$ M) of F-2 Link(Biotin) was used as the target nucleic acid polymer capturing molecule 58. This target nucleic acid polymer capturing molecule comprises nucleotides 36 to 56 of SEQ ID NO: 3, is labeled with two biotin moieties at the 5'end, and its sequence is set forth in SEQ ID NO: 4. Six different dilutions of the L2-(RP) oligonucleotide were used as target nucleic acid polymer detecting molecule 62 ($10^{-18}$ M to $10^{-13}$ M). Functioning as the target nucleic acid polymer detection molecule and target nucleic acid polymer detection molecule label, the L2-(HRP) oligonucleotide contains the complement of nucleotides 36 to 56 of SEQ ID NO: 3, is labeled with a horseradish peroxidase motif at the 5' end, and its sequence is set forth in SEQ ID NO: 6.

In FIG. 7, the mean of three independent trials was plotted with the error bars representing the standard deviation from the mean. Student's t-tests were performed, and dissimilar letters on the figure indicate responses that were statistically different ($p<0.05$). While not all levels were statistically different from one another, the response appeared to follow a linear trend. The total number of simulated cells present was calculated to be approximately 50,000 cells. This calculation was performed using the molarity of the DNA solution, the volume of sample employed (5 mL), and 6 copies of 16S rDNA/cell (based on Glaser, et al., 2001, "Comparative genomics of *Listeria* species," Science 294 (5543): 849-852). These results are consistent with experiments that used antibodies to detect live and lysed *Salmonella* and *E. coli* cells.

Figure 8:
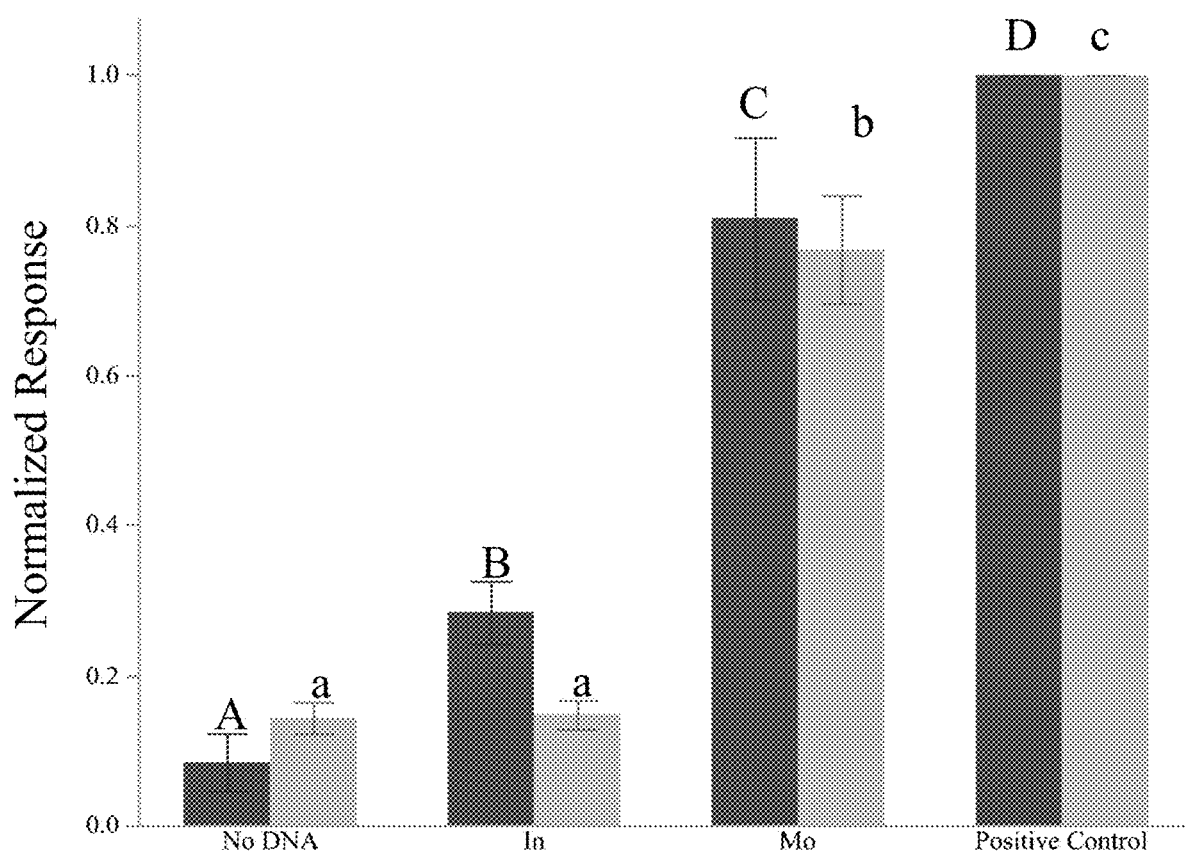
FIG. 8 depicts a graph of the sensor's normalized current response to DNA determined using either electrochemistry or absorbance.

As shown in FIG. 8, the L-2 (HRP) oligonucleotide displayed specificity for *L. monocytogenes* 16S rDNA in an assay using the flow-through electrochemical detection system of the invention. The system of the invention was exposed to a $10^{-7}$ M solution of 16S rDNA fragments from either *L. innocua* (In) or *L. monocytogenes* (Mo), and the resulting normalized current response was determined using both electrochemistry (dark bars) and absorbance (light bars). Exposure of the sensor to buffer only (no DNA) and the direct application of the polynucleotide detection molecule L-2 (RP) were used as controls. The mean response of three independent trials was plotted with the error bars representing the standard deviation from the mean, and dissimilar letters indicating statistically different ($p<0.05$) responses.

Figure 9:
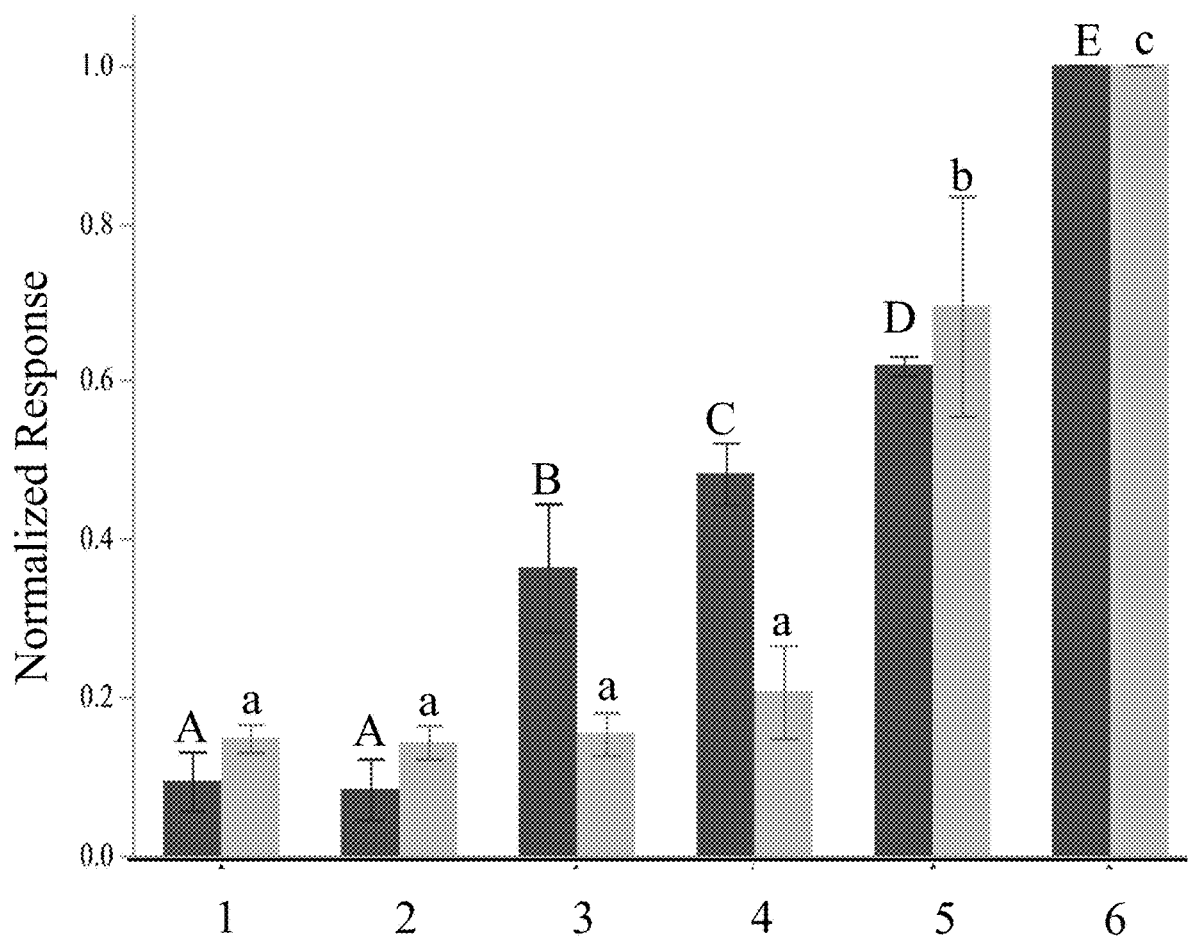
FIG. 9 depicts a graph of the sensor's normalized current response to lysed cells determined using either electrochemistry or absorbance

As shown in FIG. 9, the normalized current response of the flow-through electrochemical detection system was capable of specifically detecting *L. monocytogenes* in lysed cells at the lowest detection level tested ($10^5$ cells in a 5 mL sample). This figure also shows that absorbance measurements were not as sensitive as the electrochemical measurements. The normalized response was determined using electrochemical measurements (dark bars) and absorbance measurements (light bars) upon exposure of the working electrode to a series of lysed *L. monocytogenes* cells (ranging from $10^5$-$10^7$ cells) in a 5 mL sample volume. 1 shows results from reactions not containing polynucleotide capturing oligonucleotides (negative control); 2 shows results in the absence of cells (buffer only; no cells); 3 shows results for $10^5$ cells; 4 shows data for $10^6$ cells; 5 shows data for $10^7$ cells; and 7 shows the results for the direct application of the target nucleic acid polymer detection molecule to the sensor (positive control). The mean response from three independent trials was plotted with the error bars representing the standard deviation from the mean. Student's t-tests were performed and samples with dissimilar letters indicate responses that were statistically different (p<0.05). The data in this figure shows that it is possible to differentiate the electrochemical response generated from the exposure of the working electrode to all three dilutions of cells using student's t-tests (p<0.0076). Unlike the electrochemical response, the response measured via absorbance for the lower dilutions of cells tested could not be differentiated. However, the response generated from the positive control, the negative control, and the sample containing $10^7$ lysed cells were determined to be significantly different (p<0.003). These results once again demonstrated a higher sensitivity for electrochemical measurements as compared to the absorbance measurements.

In an embodiment, the sample's flow-through rate can range between approximately 5 mL/hour to approximately 1000 mL/hour. In another embodiment, the sample's flow-through rate can range between approximately 0.0001 mL/hour and approximately 100 liters/hour. One of ordinary skill in the art recognizes that the working electrode's volume and the flow-through rate of the sample through the assay reaction chamber can vary independently of each other. Flow rate also is impacted by the sample's viscosity. One of ordinary skill in the art is able to determine the optimal volume and rate for a specific sample and target polynucleotide. In one embodiment, a working electrode having approximately 10 mL volume and a flow-through rate of approximately 5 mL/hour is a good starting point for determining the optimal conditions for a specific sample and target nucleic acid polymer. One of ordinary skill in the art recognizes that the concentration and size of particulate matter in a sample will place constraints on the pore size, pore size distribution, and total porosity of the working electrode and one may need to filter the sample (as discussed above) or alter one or more of the working electrode's characteristics to control the sample's flow rate. When the working electrode is approximately 40% porous, then approximately 80% of the sample is contained within the porous membrane. When $\Sigma$Apores<Aoutlet the flow rate will be dictated by the electrode (porosity, diameter, height), and when $\Sigma$Apores>Aoutlet the flow rate is dictated by the area of the egress opening. In addition, the flow control valve 140 and/or the pump 120 can be adjusted to control the sample's flow-through rate. One of ordinary skill in the art can determine the optimal flow-through rate based on the user's needs.

The diameters of the assay reaction chamber's ingress opening 42, egress opening 44, pipes 38, flow control valve 30, and pump 24, can impact the height of the sample within the assay reaction chamber 28. In one embodiment, the diameter of the pipes throughout the system and the assay reaction chamber are constant and approximately the same size. In an alternative embodiment, the diameter of the pipes at various locations within the system may vary and the diameter of the assay reaction chamber's egress opening may differ from the diameter of the assay reaction chamber and/or its ingress opening.

In an embodiment, the assay reaction chamber's diameter can range from about 0.1 mm to about 500 mm. In another embodiment, the assay reaction chamber's diameter can range from about 5 mm to about 50 mm. In another embodiment, the assay reaction chamber's diameter can range between about 11 mm to about 30 mm. The diameter of the egress opening 44 can range from about 0.01 mm to about 100 mm, from about 0.1 mm to about 50 mm, from about 1 mm to about 5 mm, in various embodiments. In another embodiment, the egress opening's diameter is about 3 mm. Egress opening with different sized diameters can be paired with the different electrode configurations. The size/volume of the assay reaction chamber can range from about 0.5 mL to about 10 mL. In alterative embodiments, the volume of the assay reaction chamber can range from about 0.01 mL to about 100 mL. In one embodiment, the working electrode's diameter is the same as or slightly larger than the assay reaction chamber's egress opening's diameter so that the working electrode does not exit the assay reaction chamber into the pipe attached to the egress opening.

In an embodiment, the flow-through electrochemical detection system is operated at room temperature. In alternative embodiments, the system (or parts of the system) may be used at different temperatures, either higher or lower than room temperature. When using an enzyme (for example, horseradish peroxidase) to generate an electric current when the target polynucleotide is present, one of ordinary skill in the art recognizes that enzymatic activity generally doubles every 10° C. until the temperature reaches approximately 55° C. Thus, in some embodiments, one may add a heating element to the assay reaction chamber or utilize other methods well-known in the art to increase the temperature of the system, or just the assay reaction chamber (especially after the analyte detector has attached to the analyte) to approximately 50° C. which would enhance the chemical or enzymatic reaction that generates the measured current. In an alternative embodiment, when one is using oligonucleotides as the polynucleotide capturing molecules to capture a target polynucleotide, one of ordinary skill in the art can determine the optimal temperatures for denaturing and annealing of DNA or RNA to the polynucleotide capturing molecule. Thus, in this embodiment, one of ordinary skill can determine these different temperatures, and heat and/or cool, as necessary using known in the art methods, the system and/or the assay reaction chamber to optimize the capture and detection of the analyte.

Definitions

As used herein, "target nucleic acid polymer" refers to a nucleic acid polymer of interest in a sample. The target nucleic acid polymer may be, for example, at least one of RNA, DNA, a mixed nucleotide, an antisense RNA or DNA, a short interfering RNA (siRNA), a microRNA (miRNA), an aptamer, a SPIEGELMER synthetic L-oligonucleotide aptamer, or a peptide nucleic acid. The target nucleic acid polymer may be from any organism such as an animal (vertebrate or invertebrate), a plant or plant part, a fungus, an alga, or a microorganism. The microorganism may be a bacterium, a virus, a fungus, a parasite, or a yeast.

As used in the Examples, the target nucleic acid polymer may be a *Listeria* polynucleotide. *Listeria* is a foodborne pathogen that is known to contaminate many ready-to-eat products. Its ability to survive and replicate at 4° C. makes foods that may be refrigerated for long periods of time without heating prior to consumption especially problematic. Currently, twenty different species of *Listeria* have been characterized, these include: i L. aquatica, L. booriae, L. cornellensis, L. costaricensis, L. goaensis, L. fleischmannii, L. floridensis, L. grandensis, L. grayi, L. innocua, L. ivanovii, L. marthii, L. monocytogenes, L. newyorkensis, L. riparia, L. rocourtiae, L. seeligeri, L. thailandensis, L. weihenstephanensis, and *L. welshimeri*. Although multiple species can be found on food products, *L. monocytogenes* has been found to be the causal agent of human illness. Therefore, for food safety measures, it is important to differentiate

*L. monocytogenes* from the other *Listeria* species that may be present in foods. This is not always a simple task however, especially when trying to distinguish *L. monocytogenes* from *L. innocua*. Because of the similarities amongst the two species, errors can result when using known phenotypic tests. The existence of these challenges has created a need for fast and reliable detection methods that can specifically detect *L. monocytogenes* without a reliance upon antibodies or phenotypic differentiation. FIG. 6 presents a nucleotide alignment of the 16S rRNA region from *L. ivanovii* (Iv; set forth in SEQ ID NO: 1), *L. innocua* (In; set forth in SEQ ID NO: 2), and *L. monocytogenes* (Mo; set forth in SEQ ID NO: 3). Nucleotides that differ amongst the species are boxed.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

As used herein, the term "sample" relates to a liquid that can be water, a solution, or a suspension. In some embodiments of the invention, the sample may be from any organism such as an animal (vertebrate or invertebrate), a plant or plant part, a fungus, an alga, or a microorganism. The microorganism may be a bacterium, a virus, a fungus, a parasite, or a yeast. The sample may be liquified by itself or liquified with at least one added liquid such as water, oil, etc. In certain embodiments, the sample may be a food liquified by itself or liquified with at least one added liquid such as water, oil, etc. The sample may be raw food or cooked food, and may be obtained from plants or animals. The sample may also be obtained from the environment (e.g., water/liquid obtained from a stream, a rivers, a lake, an ocean, rain, a waste pond, a cooling pond, a mine, etc.), bodily fluids, liquified bodily tissue, or liquified prepared foods such as peanut butter, ice cream, etc.

As used herein, a "target nucleic acid polymer detecting molecule" refers to a molecule that binds the target nucleic acid polymer and transmits a signal to the working electrode so that the target nucleic acid polymer may be detected. The target nucleic acid polymer detecting molecule may be an oligonucleotide, a polynucleotide, a peptide, or a protein. The target nucleic acid polymer detecting molecule may transmit the signal once it is bound to the target nucleic acid polymer, or may be labeled with a "target nucleic acid polymer detecting molecule label" that will transmit the signal. The target nucleic acid polymer-detecting molecule may be labeled with a radioactive phosphate, biotin, a fluorophore, or an enzyme. The target nucleic acid polymer detecting molecule label may be a radioactive phosphate, biotin, a fluorophore, or an enzyme. The target nucleic acid polymer-detecting molecule or the target nucleic acid polymer-detecting molecule label can comprise an enzyme (horseradish peroxidase (HRP) was used in the examples, but other non-limiting enzyme examples include glucose oxidase, alkaline phosphatase, β-galactosidase, glucoamylase, urease, malate dehydrogenase, and glucose-6-phosphate dehydrogenase). In the examples, a chemical (3,3',5,5'-tetramethylbenzidine (TMB)) reacts with HRP to generate an electric current. Examples of other chemicals that could be used are various phenols, ammonia, NAD+, glucose, ferrocene, alkaline phosphatase, 2-aminophenol, etc.

As used herein, the term "potentiostat" relates to an electronic instrument that controls the voltage difference between a Working electrode and a Reference electrode. The potentiostat implements this control by injecting current into the cell through a Counter electrode. The potentiostat measures the current flow between the Working electrode and the Counter electrode. The controlled variable in a potentiostat is the cell potential and the measured variable is the cell current. The potentiostat determines the electron charge potential (or current) across the working electrode, thus determining the amount of target nucleic acid polymer (if any) present in the sample. The potentiostat is in electronic communication with at least one computer processor and electronic display which indicates the current. The current produced by the reaction can be compared to the current known for specific amounts of target polynucleotide, thereby enabling one to determine the amount of target nucleic acid polymer present in the sample.

As used herein, the term "working electrode" refers to the electrode on which the reaction of interest is occurring. In the instant invention, the working electrode is a porous electron conductive material, and thus an electron transducer. The working electrode may be a conductive polymer-carbon allotrope, for example, a polymer containing graphite that percolates (e.g., graphite felt).

As used herein, the term "counter electrode" refers to an electrode that provides a circuit over which current is either applied or measured. The potential of the auxiliary electrode is usually not measured and is adjusted so as to balance the reaction occurring at the working electrode. This configuration allows the potential of the working electrode to be measured against a known reference electrode without compromising the stability of that reference electrode by passing current over it.

As used herein, the term "reference electrode" relates to an electrode having an accurately maintained potential, used as a reference for measurement by other electrodes. The reference electrode can include any material, compound, and element know to a person skilled in the art as functioning as a reference electrode. In some embodiments, the reference electrode includes one or more of Ag/AgCl, Hg/HgO, Hg/Hg$_2$Cl$_2$, and Hg/Hg$_2$SO$_4$.

As used herein, the term "computer processor and associated display" relates to the computer means connected to the potentiostat that processes the electrical current and displays the results. The computer processor and associated display contain means for measuring the depth of a current peak and reporting both the position of the peak (mV) and the magnitude of the current (mA or µA). To determine the amount of target nucleic acid polymer contained within a sample, a standard curve may be generated by assessing the current signal for specific concentrations of target nucleic acid polymer with multiple replicates to assess the standard deviation of the measurements. A positive control may be used (can be supplied in a kit), and the value associated with a standard curve may be recorded. Both, the signals obtained from the unknown sample and from the positive control may be used to mathematically assess the concentration of target polynucleotide in the sample through interpolation. In an alternative embodiment, software is used to determine the quantity of target nucleic acid polymer in the sample. The software may compare the output of the potentiostat for a particular target nucleic acid polymer in the sample being analyzed to pre-determined standard curves for that particular target nucleic acid polymer.

As used herein, a "filter" is a substance located upstream of the assay reaction chamber through which the sample may flow. The filter may include lava stone, pumice, zeolite, glass fibers, animal fibers (e.g., wool), synthetic fibers (such as polyvinylidene fluoride, polyimide, poly(p-xylylene), or polyesters). One of ordinary skilled in the art can use a sample's particle size distribution (PSD) to determine the geometry of the pores in the working electrode and/or the filter to accommodate suspensions with a particular size distribution of components in the mixture. One of ordinary skill in the art is aware of various methods to remove the particulate matter from the sample without removing any (or remove minute quantities of) target polynucleotide from the sample. Well-known methods of removing particulate matter from the sample involve passing the sample through a continuous flow through centrifuge, or through a fluid filter, such as a gravity filter, a pressure filter, or a vacuum filter. The fluid filter media may be made of a variety of materials including cloth, foam, carbon, sintered stainless steel, glass wool, etc.

As used herein, the term "blocking compound" refers to a compound used to help eliminate non-specific binding onto the working electrode while allowing transfer of the electric signal produced. The blocking compound may be any protein or peptide, although certain compounds perform better than others because they bind readily to nonspecific sites (also called reactive sites) at neutral pH or stabilize the function of other assay components. Bovine serum albumin (BSA), skim milk, non-fat dry milk, salmon sperm DNA, sonicated salmon sperm DNA, gelatin partial hydrolysate, polyvinyl alcohol, fish protein, hexylamine, hydroxylamine, ethanolamine hydrochloride, 1,3-propyldiamine, and mixtures thereof are some of the common blocking compounds. The specific blocking compound used is determined by the sensitivity of the of the electrochemical assay and the signal-to-noise ratio obtained. In the Examples, BSA plus sheared salmon sperm DNA was used as a blocking compound in the detection of target polynucleotides using an electrochemical biosensor. A blocking compound may be at least one of bovine serum albumin (BSA), non-fat milk, salmon sperm DNA (SSDNA), sheared SSDNA, or combinations thereof.

As used herein, the term "capture molecule" refers to a molecule bound to the working electrode to which the target nucleic acid polymer capture molecules bind. The capture molecule may be a polypeptide, such as NEUTRAVIDIN deglycosylated avidin or any molecule that may bind target nucleic acid polymer-capturing molecules.

As used herein, the term "target nucleic acid polymer capturing molecule" refers to a molecule designed to capture the target nucleic acid polymer of interest.

As used herein, the term "target nucleic acid polymer capturing molecule label" refers to a label at the 5'end or 3' end of the target nucleic acid polymer capturing molecule that facilitates its binding to the capture molecule. When the capture molecule is NEUTRAVIDIN deglycosylated avidin, the target nucleic acid polymer capturing molecule may be labeled with biotin.

As used herein, the term "target nucleic acid polymer" refers to the molecule whose presence is to be determined with the system of the invention.

As used herein, the term "target nucleic acid polymer detecting molecule" refers to a molecule that binds the target nucleic acid polymer, and when bound to the target nucleic acid polymer, directly or indirectly, generates an electrical signal.

As used herein, the term "target nucleic acid polymer detecting molecule" refers to a label on the target nucleic acid polymer detecting molecule that may be used to create an electrical signal.

As used herein, the term "processor" refers to a computer chip that receives input and provides the appropriate output.

As used herein, the term "display" refers to an output device for presentation of the supplied electrical signal in visual or tactile form. The display may be a computer monitor, a phone screen, or a tablet.

As used herein, the terms "oligo" and "oligonucleotide" are used interchangeably and refer to a single stranded, short nucleic acid molecule (containing less than 30 nucleotides).

As used herein, the term "about" is defined as plus or minus ten percent of a recited value. For example, about 1.0 g means 0.9 g to 1.1 g.

Embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby. All publications, patents, and patent applications mentioned in this specification are herein incorporated by reference to the same extent as if each individual publication, patent, or patent application was specifically and individually indicated to be incorporated by reference.

EXAMPLES

Having now generally described this invention, the same will be better understood by reference to certain specific examples, which are included herein only to further illustrate the invention and are not intended to limit the scope of the invention as defined by the claims.

Example 1

Materials and Methods

Sources of the materials used, preparation of stock solutions, and construction and use of the biochemical sensors used in the invention are described in this example.

Sourced Materials and Stock Solutions

Electrode polishing suspension and the Ag/AgCl electrodes were sourced from Bioanalytical Systems, Inc. (West Lafayette, Indiana, USA), platinum wires were acquired from VWR (Radnor, Pennsylvania, USA), molten wax were acquired from Amazon (South Lake Union; Seattle, Washington, USA), and the graphite felt (GF) utilized as the graphite felt electrode (GFE) was obtained from Electrosynthesis (Lancaster, New York, USA). NEUTRAVIDIN deglycosylated avidin was purchased from Thermo Fisher Scientific (Waltham, Massachusetts, USA), and borosilicate beads were obtained from Thomas Scientific (Swedesboro, New Jersey, USA). The 3,3',5,5'-tetramethylbenzidine (TMB), sodium acetate, glacial acetic acid, sulfuric acid, acetonitrile, TWEEN-20 polysorbate, and phosphate buffered saline tablets were all purchased from Sigma Aldrich (Billerica, Massachusetts, USA). The phosphate buffered saline (PBS) tablets were prepared according to the manufacturer's protocol to yield a 10 mM solution (pH 7.3-7.6). NANOPURE purified water was deionized in-house using a BARNESTEAD water treatment system (Barnstead International; Dubuque, Iowa, USA). HRP-labeled oligonucleotides were manufactured by BioSynthesis (Lewisville, Texas, USA). Biotin-labeled and non-modified DNA oligonucleotides were manufactured by Integrated DNA Technologies (Coralville, Iowa, USA).

An oligonucleotide containing the complement of nucleotides 36 to 56 of SEQ ID NO: 3 (AGAATAGTTTTATGG-GATTAG; set forth in SEQ ID NO: 6) was named L-2 oligo, and when modified with an HRP motif at its 5' end was named L2-(HRP) oligo. Four Cysteines were added at the 5' end of an oligonucleotide containing nucleotides 36 to 56 of SEQ ID NO: 3 to prepare the polynucleotide detecting oligonucleotide F-2 Link (CCCCCTAATCCCATAAAA CTATTCT; set forth in SEQ ID NO: 4). An oligonucleotide complementary to nucleotides 99 to 120 of SEQ ID NO: 3, L. mono 16S-Rev7 (CTGATCCACGATTACTAGCGAT; SEQ ID NO: 5). The F-2 Link and L. mono_16S-Rev7 oligonucleotides were modified with two biotins at the 5' end to create F-2 Link(Biotin) and L. mono_16S-Rev7(5Biotin).

TKMB buffer was prepared according to a method previously described (Beaudet, L., et al., 2001 "Homogeneous assays for single-nucleotide polymorphism typing using AlphaScreen," Genome Res. 11(4): 600-608). The buffer was prepared in 500 mL increments using 10 mM Tris-Cl (pH 8.0), 50 mM KCl, 4 mM $MgCl_2$, 200 μg/mL bovine serum albumin (BSA). Saline-sodium citrate (SSC) buffer was purchased as a 20× stock solution of 3 M sodium chloride and 300 mM trisodium citrate (adjusted to pH 7.0 with HCl) from Thermo Fisher Scientific (Waltham, MA USA) and diluted in TKMB. The addition of 1% (v/v) sodium dodecyl sulfate (SDS) to 0.1×SSC was used to prepare the SSC/SDS Buffer.

$TMB/H_2O_2$ solution was prepared freshly for each assay. A 0.3 mM TMB was prepared by diluting a stock solution (6 mg of TMB in 4 mL acetonitrile) in 59.6 mL of 0.20% sodium acetate buffer containing 15 mL of acetonitrile (titrated to pH 4.8-5.0 using acetic acid). Prior to use, 6.3 μL of 3% hydrogen peroxide was added per mL of TMB solution used, with the solution being protected from light until use. Assay stop solution consisted of 1 M sulfuric acid.

Flow-through, enzyme-amplified electrochemical biosensors were constructed following Capobianco, et al. (2019, "Rapid detection of Salmonella enterica serotype Typhimurium in large volume samples using porous electrodes in a flow-through, enzyme-amplified immunoelectrochemical sensor," Anal. Bioanal. Chem. 411(20): 5233-5242) with modifications. Briefly, a one-inch diameter (0.25-inch thick) circle cut from graphite felt (GF) obtained from Electrosynthesis (Lancaster, New York, USA) was utilized as the graphite felt electrode (GFE). A platinum wire (0.5 mm diameter, 2 inches in length) was used to connect the GF to the potentiostat through a via hole. The via hole was sealed with wax to form a watertight seal. NEUTRAVIDIN deglycosylated avidin (Thermo Fisher Scientific; Waltham, Massachusetts, USA) was immobilized on the GFE surface. After wetting the GFE with phosphate buffered saline (PBS) solution, the GFE was immersed in 5 mL of a $7.0\times10^{-7}$ M solution of NEUTRAVIDIN deglycosylated avidin in TKMB buffer (10 mM Tris-Cl, 50 mM KCl, 4 mM $MgCl_2$, 200 μg/mL bovine serum albumin [BSA] at pH 8.0), which was then flowed through the GFEs. The eluted solution was collected, reapplied to the GFE, and allowed to incubate for one hour. After 1 hour, the GFE was rinsed with 10 mL of PBST (0.5% TWEEN-20 polysorbate in PBS). The electrode housing for the GFE was prepared in the same manner as described.

Following the rinse with PBST, the GFE was blocked for 30 minutes with a 5 mL solution of one of the six blocking agents (BSA; Non-fat milk; Salmon sperm DNA (SSDNA); sheared SSDNA; BSA plus SSDNA; or BSA plus sheared SSDNA) before being rinsed twice with 5 mL PBST. Dehydrated powder BSA was purchased from Sigma Aldrich (Billerica, Massachusetts, USA), and was reconstituted in TKMB buffer at a concentration of 0.25 mg/mL.

Non-fat NESTLE CARNATION milk powder was purchased from a local supermarket and reconstituted in TKMB buffer at a concentration of 0.25 mg/mL. SSDNA sodium salt was purchased from Sigma Aldrich and reconstituted to 10 mg/mL in TKMB. Sheared SSDNA was produced via sonication of SSNDA at 40 kHz at room temperature in a BRANSON 2510 ultrasonic cleaner (Danbury, Connecticut, USA). The sample was exposed to a total of five (5) sonication cycles, each with a duration of 30 seconds. To avoid excessive heating 30 second intervals of no sonication were utilized in between sonication cycles. Prior to use as a blocking reagent, the SSDNA solution was diluted 1:4 in TKMB. The BSA/SSDNA blocking solution was prepared by first reconstituting the SSDNA as described above without shearing and adding powdered BSA to obtain a final concentration of 0.25 mg/mL SSDNA and 0.25 mg/mL BSA. The BSA/sheared SSDNA was produced in a fashion similar to the BSA/SSDNA except the SSDNA was sheared via sonication using the procedure described above.

A negative and a positive sample preparation were analyzed for each of the blocking agents tested using a GFE set up as shown in FIG. 3. The negative preparation determined any potential noise generated from the nonspecific binding of the detection L-2 (HRP) oligo to the GFE, while the positive preparation demonstrated the effects of the blocking reagents on the maximum signal that could be generated by the assay. For the negative sample preparation, 5 mL of a $4.30\times10^{-9}$ M L-2 (HRP) oligo (SEQ ID NO: 6) solution was passed through the GFEs. The eluted solution was collected, reapplied to the GFE, and allowed to incubate for one hour. Following elution, the GFEs were rinsed twice with 5 mL SSC/SDS warmed to 50° C. For the positive control, a 5 mL solution of the $TMB/H_2O_2$ solution containing $4.30\times10^{-9}$ M L-2 (HRP) oligo (SEQ ID NO: 6) was made. This was applied directly to the GFE without rinsing/elution, producing the maximum possible signal that could be generated by the HRP.

The TMB solutions for all the blocked and positive control samples were allowed to react for 20 minutes at room temperature in the dark, followed by the addition to the container of 5 mL of 1 M $H_2SO_4$ stop solution. Five minutes following the addition of the stop solution, the stop solution was eluted, and the molten wax from the via hole in the assay reaction chamber was removed to allow insertion of the platinum counter electrode into the drilled hole for contact with the GFE. The hole was resealed with molten wax and the eluent was placed back into the tube containing the GFE. Glass beads were added to compress the GFE to ensure that continuous contact was made with the platinum wire lead and the electrochemical measurements were recorded using a BAS 100B/W electrochemical analyzer (Bioanalytical Systems, Inc.; West Lafayette, Indiana, USA) in the range of −1200 mV to 1200 mV with a sensitivity of 100 mA/V.

Except for the experiments described in Example 2, the surface of the GFEs for all remaining experiments was coated with a biotin-labeled capture oligo. As stated above, the 5' end of each of the capture oligos was modified with two biotins to prepare, F-2 Link(Biotin) and L. mono_16S-Rev7(5Biotin). Addition of two biotins was expected to increase the stability of the biotin NEUTRAVIDIN deglycosylated avidin bond at higher temperatures (Dressman, D., et al., 2003, "Transforming single DNA molecules into fluorescent magnetic particles for detection and enumeration of genetic variations," Proc. Natl. Acad. Sci. U.S.A 100(15):

8817-8822). A 2.0×10⁻⁸ M solution of the biotinylated capture oligos was prepared in TKMB. The solution was then passed through the NEUTRAVIDIN deglycosylated avidin coated GFEs that were blocked with BSA/sheared SSDNA as described above. The effluent was subsequently returned to the vessel containing the GFE and incubated for one hour. Following the one hour incubation, the solution was again passed through the GFEs, and the graphite felt electrodes were rinsed 2 times with 5 mL SSC/SDS warmed to 50° C. After rinsing, the GFE's were stored at 4° C. until utilized.

To determine the level of nucleic acid strands captured by the GFE, a polynucleotide detecting molecule consisting of an oligonucleotide conjugated with a single HRP enzyme was utilized. This polynucleotide detecting molecule had the ability to bind to its complementary sequence and to provide a moiety that could be converted into a detectable signal for the sensor. Five milliliters (5 mL) of $9.24 \times 10^{-9}$ M L-2 (HRP) oligo (SEQ ID NO: 6) in TKMB was passed through a GFE coated with blocking compound, coated with polynucleotide capturing oligonucleotides. The effluent was collected and then reapplied to each respective GFE and incubated at room temperature for 1 hour. Following elution, the GFEs were rinsed with 2×5 mL SSC/SDS warmed to 50° C.

Next, 5 mL of a TMB/$H_2O_2$ solution was applied to the GFEs and allowed to react for 20 minutes in the dark. Then, 5 mL of 1 M $H_2SO_4$ stop solution was added to the container. Five minutes following the addition of the stop solution, the stop solution was eluted, and the molten wax covering the drill hole was removed to allow insertion of platinum counter electrode into the GFE via the drilled hole. The hole was resealed with molten wax and the eluent was placed back into the tube containing the GFE. Glass beads were added to compress the GFE and ensure continuous contact with the platinum wire lead so that the electrochemical measurements could be recorded with the BAS 100B/W electrochemical analyzer. Colorimetric measurements at an absorbance wavelength of 450 nm by a SAFIRE2 plate reader (Tecan Group Ltd.; Männedorf, Switzerland) were also recorded. Absorbance measurements and electrochemical measurements were conducted on the same day, with the absorbance measurements being conducted first.

Positive controls consisted of 5 mL $9.24 \times 10^{-9}$ M L-2 (HRP) in TMB/$H_2O_2$, which was applied directly to the GFE without any subsequent wash/elution steps. The solution was allowed to incubate for 20 minutes in the dark, after which 5.0 mL of the 1M $H_2SO_4$ stop solution was added. Five minutes following the addition of the stop solution, the electrochemical measurement was recorded. Negative controls received the same treatment as the experimental samples except that no polynucleotide-capturing molecule was utilized. Throughout the analysis, the GFE associated with the positive and the negative controls were not exposed to any biotinylated oligos.

Signal-to-noise ratios were calculated by dividing the positive control by the negative control collected within a specific trial. Trials were performed in triplicate, and the resulting responses were reported as the average of the three trials.

The current measured by the BAS 100B/W was reported at −300 mV. To minimize the variability associated with the batch-to-batch variation of oligo-enzyme conjugate, and the degradation of hydrogen peroxide, TMB solution was prepared daily, and the current of each measurement was normalized by dividing the obtained value by the value of the positive control for that trial.

Example 2

Blocking Agent Selection

The effects of different blocking agents on the signal to noise ratio and on the absorbance at 450 nm of a graphite working electrode were determined. The blocking agents tested were BSA; non-fat milk; salmon sperm DNA (SSDNA); sheared SSDNA; BSA/SSDNA; and BSA/ sheared SSDNA.

The surface area of the graphite felt is extremely large and contains both functional areas for selective binding, as well as inactive areas. In food safety diagnostics, the surfaces utilized in testing platforms often come into contact with complex mixtures and may be prone to non-specific and potentially irreversible adherence of mixture components leading to a phenomenon commonly referred to as non-specific adsorption (NSA). Thus, initial work was conducted to identify conditions that maximized the signal associated with the selective binding of target polynucleotides to the capture surface while minimizing the signal associated with NSA.

To test the effectiveness of the different blocking agents, a working electrode 46 was coated with NEUTRAVIDIN deglycosylated avidin (capture molecule 54), and one of the different blocking compounds 52 tested, in the absence of a nucleic acid polymer capturing molecule 58, or a target nucleic acid polymer 60. Negative sample preparations consisted of 5 mL of a $4.30 \times 10^{-9}$ M L-2 (HRP) solution applied to the GFE and rinsed prior to incubation with the TMB substrate solution. This system allowed assessing the signal produced by non-specific adsorption of the L-2 (HRP) oligo. Positive sample preparations consisted of $4.30 \times 10^{-9}$ M L-2 (HRP) directly added to the TMB substrate without rinsing. This system allowed assessing the maximum signal intensity.

The effects of BSA; non-fat milk; salmon sperm DNA (SSDNA); sheared SSDNA; BSA/SSDNA; or BSA/sheared SSDNA as potential blocking agents on the assay signal were determined. In FIG. 4 and FIG. 5, the blocking agents tested are presented as categorical variables along the x-axis and the signal-to-noise ratios are presented on the y-axis. The signal-to-noise ratios for the electrical currents generated using the flow through electrochemical sensor are shown in FIG. 4, and the corresponding absorbance readings at 450 are shown in FIG. 5 The mean of three independent trials was plotted with the error bars representing the standard deviation. Significance was measured using Students t-tests ($p<0.05$). In FIG. 4 and FIG. 5 dissimilar letters represent statistical differences amongst samples.

These results indicated that nonfat milk is not the optimal blocking agent for assays using oligo fragments. As seen in FIG. 4 and FIG. 5, when using an oligonucleotide bound to HRP as the polynucleotide detection molecule, the measured signal-to-noise ratio was higher for BSA+ sheared SSDNA for both the flow-through electrochemical assay ($p<0.001$) and the absorbance assay ($p<0.0001$). These data also indicated that while there was a good deal of similarity between the performance of the blocking agents in the two assays, the flow-through electrochemical assay was more sensitive than the absorbance assay to the blocking agent used. This is because the measured responses between all of the experimental factors are statistically significant ($0.001<p<0.003$) for the electrochemical measurements, while several of the absorbance measurements (such as BSA+ sheared SSDNA compared to BSA alone and BSA+ not sheared SSDNA compared to sheared SSDNA or nonfat milk alone) cannot be differentiated by a Students t-test with p<0.05.

This example shows that when using a GFE to determine the presence of target polynucleotides in a sample, the most appropriate blocking agent is BSA+ sheared SSDNA. BSA+ sheared SSDNA was selected to be the blocking agent utilized throughout the remaining examples.

Example 3

Polynucleotide Detection

To assess the capability of a graphite working electrode to detect L. monocytogenes DNA As stated above, an oligonucleotide with known specificity for the 16S rRNA region of L. monocytogenes (Wang, Cao, & Johnson, 1992) was modified with a single HRP at the 5'end to allow for the detection of DNA from L. monocytogenes. This capture oligo is referred to as L-2 (HRP). FIG. 6 depicts a nucleotide alignment of the 16rRNA region of L. ivanovii (nucleotides 1242 to 1361 GenBank accession No. JF967631; set forth in SEQ ID NO: 1), L. innocua (nucleotides 1256 to 1375 of GenBank accession No. S55473; set forth in SEQ ID NO: 2), and L. monocytogenes (nucleotides 2625398 to 265515 of GenBank accession No. AE017262; set forth in SEQ ID NO: 3). This alignment showed that the L. ivanovii and in L. innocua nucleotide sequences of this 16S rRNA region are identical, while there are four nucleotides that are different in L. monocytogenes. As stated above, the polynucleotide detecting oligo L-2 (RP) binds to nucleotides 36 to 56 of SEQ ID NO: 3. This region contains two of the single nucleotide polymorphisms that permit the differentiation of L. monocytogenes from the other closely related Listeria species. As stated above, the F-2 Link (SEQ ID NO: 4) capture oligo was modified by adding two biotin motifs at the 5' end to allow for its conjugation to the NEUTRAVIDIN deglycosylated avidin-coated surface of the GFE.

The ability of the flow-through, enzyme-amplified electrochemical sensor to produce a signal when oligos were utilized as the biorecognition element for the assay was ascertained. To test this, the F-2 Link (Biotin) oligo (SEQ ID NO: 4) bound to the NEUTRAVIDIN deglycosylated avidin was used as the capture oligo, and the L2 (HRP) oligo (SEQ ID NO: 6), was used as the detection oligo. The F2 Link (Biotin) oligo (SEQ ID NO: 4) comprises the complement of nucleotides 1 to 21 of the L2 (RP) oligo (SEQ ID NO: 6).

To define the limit of detection, signals generated by the flow-through, enzyme-amplified electrochemical sensor using six different dilutions of L-2 (RP) oligo ($10^{-18}$ to $10^{-13}$ M) and a constant amount of F-2 Link (Biotin) ($2.0 \times 10^{-4}$ M) were recorded. The normalized current responses were graphed, and are shown in FIG. 7. This graph shows that a response that was dependent upon the concentration of L-2 (HRP) with a limit of detection of $1 \times 10^{-16}$ M (p=0.0474). While not all levels were statistically different from one another, the response appeared to follow a linear trend. Using the molarity of the DNA solution, the 5 mL sample volume employed, and the fact that there are 6 copies of 16S rDNA/cell (Glaser, P., et al., 2001, "(2001). Comparative genomics of Listeria species," Science 294(5543): 849-852), the total simulated number of cells present was predicted to be approximately 50,000 cells. These results are consistent with previous experiments that used antibodies to detect live and lysed Salmonella and E. coli cells (Capobianco, J. A., et al., 2020, "Detection of pathogenic bacteria in large volume food samples using an enzyme-linked immunoelectrochemical biosensor," Food Control 1119 107456; Capobianco, J. A., et al., 2019 (Supra)).

Example 4

Specific Detection of L. Monocytogenes Polynucleotides

Specific detection of L. monocytogenes using the system of the invention.

In order for the assay to be employed as a detection tool for L. monocytogenes, an alternative capture oligo that would not directly bind the detection oligo needed to be assimilated into the assay design. While not specific to L. monocytogenes, this capture oligo, known as L. mono_16S-Rev7 (5Biotin) (SEQ ID NO: 5), bound to a region 43 nucleotides downstream of the L-2 (RP) oligo, and tethered Listeria 16S rDNA fragments to the GFE. However, only tethered L. monocytogenes 16S rDNA fragments could ultimately serve as a bridge that enabled detection via the specific binding of the L-2 (RP) oligo (FIG. 3). To ensure that all of the conditions necessary for signal generation had been met, and that the L-2 (HRP) oligo would be specific for the detection of L. monocytogenes, single-stranded ULTRAMER DNA fragments containing the aforementioned regions were synthesized based upon the known 16S rDNA sequences for both L. monocytogenes (set forth in SEQ ID NO: 7) and L. innocua (set forth in SEQ ID NO: 8). These synthesized fragments were 195 nucleotides in length and were applied individually at a concentration of $10^{-13}$ M to GFEs that had been conjugated with the L. mono_16S-Rev7 (5Biotin) oligo and blocked with BSA+ sheared SSDNA. After washing the GFEs with a solution of SSC/SDS warmed to 50° C. to help eliminate non-specific binding, and to remove any untethered DNA, electrochemical signals generated by the presence of the HRP and the absorbance at 450 nm were recorded. Graphs of the normalized responses are shown in FIG. 8, where the normalized electrochemical signal is presented as dark gray bars, and the normalized absorbance responses are presented as light gray bars. As a negative control, the same protocol was followed with the exception that the blocked GFE was not exposed to any additional DNA. The positive control consisted of a direct application of the L-2 (HRP) oligo with subsequent exposure to the TMB substrate, without any wash steps, to define the maximum signal that could be produced by the amount of HRP presented in the protocol. Students t-tests were conducted to compare the signal generated using the different experimental treatments. The response generated post exposure to the L. monocytogenes 16S rDNA fragment can be differentiated from the response generated from the L. innocua 16S rDNA fragment, and from the no DNA control by both absorbance and electrochemical responses (p<0.0001). This indicates that the L-2 (HRP) oligo displays specificity for the identified portion of the L. monocytogenes 16S rDNA. Given that the response generated with L. innocua is significantly different from that generated in the total absence of DNA in the electrochemical assay (p=0.0039) suggests that a low level of cross-reactivity likely exists. In addition, the fact that the absorbance measurements for these same samples was not significantly different (p=0.9025) can be explained by previous observations that the response obtained via electrochemistry is more sensitive than that obtained via absorbance.

Example 5

Detection of L. *Monocytogenes* Cells

The ability of the sensor to detect *L. monocytogenes* cells was subsequently tested using a 10-fold dilution series of *L. monocytogenes* (FIG. 9)

GFEs containing the L. mono_16S-Rev7 (5Biotin) oligo (seq id no: 5) immobilized to the surface through NEUTRA-VIDIN deglycosylated avidin were exposed to $10^5$, $10^6$, or $10^7$ lysed *L. monocytogenes* F2365 cells in 5 mL sample volumes. The number of cells used to inoculate the experimental samples was verified using the 6×6 drop plate method. The negative control utilized an identical protocol with the exception that L. mono_16S-Rev7 oligo was not bound to the capture polypeptide. This negative control was still exposed to $10^7$ lysed cells, which helped to determine the presence of non-specific binding by the genomic DNA. To test for binding of the detection oligonucleotide in the absence of *L. monocytogenes* DNA, a no cells control consisting of a GFE containing the L. mono_16S-Rev7 (5Biotin) bound to the capture polypeptide, but not exposed to any cellular material was performed. The positive control consisted of a direct application of an L-2 (HRP) oligo solution to the GFE as described in Example 2, above. The normalized current response was determined using both electrochemistry and absorbance upon exposure of the sensor to the series of lysed *L. monocytogenes* cells. FIG. 9 presents the normalized response graphs, where the electrochemistry data is shown by dark grey bars, and the absorbance data is shown by light grey bars. Exposure of the sensor to buffer only (no cells), sensors that did not contain capture oligo (negative control), and the direct application of the detection oligo to the sensor (positive control) were also performed. The mean response from three independent trials is plotted with the error bars representing the standard deviation from the mean. Students t-tests were performed and samples with dissimilar letters indicate responses that were statistically different ($p<0.05$). The data in this figure shows that the Absorbance data was not significantly different for the negative control, the no cells control, the $10^5$ cells, and the $10^6$ cells, while the electrochemical measurements were able to statistically differentiate between the negative control, the no cell control, and $10^5$ cells.

The electrochemical response generated from the exposure of the GFE to all three dilutions of cells can be differentiated using students t-tests ($p<0.0076$). Unlike the electrochemical response, the response measured via absorbance for the lower dilutions of cells tested could not be differentiated. However, the response generated from the positive control, the negative control, and the sample containing $10^7$ lysed cells were determined to be significantly different ($p<0.003$). These results once again demonstrated a higher sensitivity for electrochemical as compared to absorbance measurements.

---

We claim:

1. A system for detecting target nucleic acid polymers in a sample, the system comprising: at least one assay reaction chamber, each reaction chamber comprising one porous working electrode through which the sample flows, an ingress opening, through which the sample is capable of entering the assay reaction chamber, and an egress opening, through which the sample is capable of exiting the assay reaction chamber, wherein the porous working electrode forms a barrier between the ingress opening and the egress opening such that the sample must traverse through the barrier to reach the egress opening; a plurality of target nucleic acid polymer-capturing molecules complementary to a first portion of the target nucleic acid polymer in the sample, the plurality of nucleic acid polymer-capturing molecules bound to the porous working electrode, and positioned within the assay reaction chamber, free within the assay reaction chamber a substrate and a plurality of polynucleotide or oligonucleotide target nucleic acid polymer-detecting molecules comprising a protein label and complementary to a second portion of the target nucleic acid polymers in the sample, and an electrical measuring device, wherein the system is structured so that as the sample flows through the porous working electrode by gravity, target nucleic acid polymer-capturing molecules bind to the first portion of any target nucleic acid polymers present in the sample; after the sample flows through the working electrode the substrate and the plurality of target nucleic acid detecting molecules are added to the reaction chamber, target nucleic acid polymer-detecting molecules bind to the second portion of any target nucleic acid polymers bound to target nucleic acid polymer-capturing molecules bound to the working electrode, a measurable electrical current is generated by the protein label and is transmitted to the electrical measuring device, the presence of the electric current indicating a presence of the target nucleic acid polymers in the sample.

2. The system of claim 1, further comprising a blocking compound bound to the porous working electrode and positioned within the at least one assay reaction chamber.

3. The system of claim 2, wherein the blocking compound is at least one of bovine serum albumin (BSA), non-fat milk, salmon sperm DNA (SSDNA), BSA/SSDNA, BSA/sheared SSDNA, or sheared SSDNA.

4. The system of claim 1, further comprising a flow control valve in fluid communication with the assay reaction chamber, wherein the flow control valve controls the sample's flow rate through the porous working electrode.

5. The system of claim 4, further comprising a waste reservoir in fluid communication with the flow control valve.

6. The system of claim 1, further comprising a sample reservoir upstream of the assay reaction chamber, and in fluid communication with the assay reaction chamber.

7. The system of claim 6, further comprising a filter upstream of the assay reaction chamber and in fluid communication with the sample reservoir and the assay reaction chamber.

8. The system of claim 1, further comprising a pump, wherein the pump is in fluid communication with the assay reaction chamber.

9. The system of claim 1, further comprising a reference electrode and a counter electrode; and the assay reaction chamber further comprising a first opening in a wall of the assay reaction chamber for the reference electrode to be in electronic communication with the electrical measuring device via a first connector, and a second opening in the wall of the assay reaction chamber for the counter electrode to be in electronic communication with the electrical measuring device via a second connector, wherein the first opening is filled with an electronic fill material.

10. The system of claim 1, wherein the electrical measuring device comprises a potentiostat.

11. The system of claim 1, wherein the target nucleic acid polymer molecule in the sample is RNA, DNA, a mixed nucleotide, an antisense RNA, an antisense DNA, a short interfering RNA (siRNA), a microRNA (miRNA), an aptamer, a synthetic L-oligonucleotide, or a peptide nucleic acid.

12. A method for detecting a target nucleic acid polymer in a sample, the method comprising: passing the sample containing target nucleic acid polymers through the working electrode in the assay reaction chamber of the system of claim 1, where a plurality of target nucleic acid polymer-capturing molecules bound to the porous working electrode bind to a first portion of any target nucleic acid polymer in the sample, passing target nucleic acid polymer-detecting molecules comprising a protein label through the working electrode, wherein the target nucleic acid polymer-detecting molecules bind to a second portion of the target nucleic acid polymer bound to the target nucleic acid polymer-capturing molecules bound to the porous working electrode, and performing a reaction with the label on the target nucleic acid polymer-detecting molecules and a substrate to generate an electrical current, wherein the electrical current is measured by the electrical measuring device, indicating the presence of the target nucleic acid polymer in the sample.

13. The method of claim 12, wherein the target nucleic acid polymer is from an animal, a plant or plant part, a fungus, an alga, or a microorganism.

14. The method of claim 12, wherein the method further comprises binding a blocking compound to the working electrode.

15. The system of claim 1, wherein target nucleic acid polymer-capturing molecules bound to the porous working electrode comprise consisting of a modified polynucleotide of nucleotide sequence of SEQ ID NO: 6, and the target nucleic acid polymer-detecting molecules consisting of a modified polynucleotide of nucleotide sequence of SEQ ID NO: 5.

16. The method of claim 12, wherein target nucleic acid polymer-capturing molecules bound to the porous working electrode consisting of a modified polynucleotide of nucleotide sequence of SEQ ID NO: 6, and the target nucleic acid polymer-detecting molecules consisting of a modified polynucleotide of nucleotide sequence of SEQ ID NO: 5.

17. The system of claim 1, wherein the porous working electrode is located on a bottom of the assay reaction chamber and spans the assay reaction chamber such that the porous working electrode surrounds the egress opening.

18. The system of claim 9, further comprising a bonding pad screen-printed over the electronic fill material on an outside of the assay reaction chamber; and wherein the electronic fill material is a conductive epoxy.

\* \* \* \* \*

SEQUENCE LISTING

```
<160> NUMBER OF SEQ ID NOS: 7

<210> SEQ ID NO 1
<211> LENGTH: 120
<212> TYPE: RNA
<213> ORGANISM: Listeria ivanovii

<400> SEQUENCE: 1
gaugguacaa agggucgcga agccgcgagg uggagccaau cccauaaaac cauucucagu      60
ucggauugua ggcugcaacu cgccuacaug aagccggaau cgcuaguaau cgcggaucag    120

<210> SEQ ID NO 2
<211> LENGTH: 120
<212> TYPE: RNA
<213> ORGANISM: Listeria innocua

<400> SEQUENCE: 2
gaugguacaa agggucgcga agccgcgagg uggagccaau cccauaaaac cauucucagu      60
ucggauugua ggcugcaacu cgccuacaug aagccggaau cgcuaguaau cguggaucag    120

<210> SEQ ID NO 3
<211> LENGTH: 120
<212> TYPE: RNA
<213> ORGANISM: Listeria monocytogenes

<400> SEQUENCE: 3
gauaguacaa agggucgcga agccgcgagg uggagcuaau cccauaaaac uauucucagu      60
ucggauugua ggcugcaacu cgccuacaug aagccggaau cgcuaguaau cguggaucag    120

<210> SEQ ID NO 4
<211> LENGTH: 25
<212> TYPE: DNA
<213> ORGANISM: Artificial Sequence
```

```
<220> FEATURE:
<223> OTHER INFORMATION: Chemically Synthesized

<400> SEQUENCE: 4 cccctaatc ccataaaact attct                                              25

<210> SEQ ID NO 5
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 5
ctgatccacg attactagcg at                                                22

<210> SEQ ID NO 6
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 6
agaatagttt tatgggatta g                                                 21

<210> SEQ ID NO 7
<211> LENGTH: 195
<212> TYPE: DNA
<213> ORGANISM: Listeria innocua

<400> SEQUENCE: 7
gacgtcaaat catcatgccc cttatgacct gggctacaca cgtgctacaa tggatggtac       60
aaagggtcgc gaagccgcga ggtggagcca atcccataaa accattctca gttcggattg      120
taggctgcaa ctcgcctaca tgaagccgga atcgctagta atcgtggatc agcatgccac      180
ggtgaatacg ttccc                                                       195
```